United States Patent
Dixit et al.

(10) Patent No.: US 6,447,756 B1
(45) Date of Patent: *Sep. 10, 2002

(54) DESENSITIZING DUAL COMPONENT DENTIFRICE

(75) Inventors: Nagaraj Dixit, Plainsboro, NJ (US); Kowsilla P. Pillay, New York, NY (US); Robert J. Gambogi, Belle Mead, NJ (US)

(73) Assignee: Colgate Palmolive Company, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/708,167

(22) Filed: Nov. 8, 2000

(51) Int. Cl.$^7$ .................................................. A61K 7/16
(52) U.S. Cl. ....................................................... 424/49
(58) Field of Search ..................................... 424/49–58

(56) References Cited

U.S. PATENT DOCUMENTS

| | | | | |
|---|---|---|---|---|
| 4,181,633 A | * | 1/1980 | Colodwey et al. | 252/525 |
| 4,581,217 A | * | 4/1986 | Shinpo et al. | 423/339 |
| 4,645,662 A | * | 2/1987 | Makashima et al. | 424/52 |
| 4,738,838 A | * | 4/1988 | Shinpo et al. | 423/339 |
| 4,992,258 A | * | 2/1991 | Mason | 424/49 |
| 5,374,417 A | * | 12/1994 | Norfleet et al. | 424/49 |
| 5,589,159 A | * | 12/1996 | Markowitz et al. | 424/49 |
| 5,603,920 A | * | 2/1997 | Rice | 424/49 |
| 5,651,958 A | * | 7/1997 | Rice | 424/49 |
| 6,106,812 A | * | 8/2000 | Prencide et al. | 424/53 |
| 6,180,089 B1 | * | 1/2001 | Gambogi et al. | 424/52 |
| 6,290,933 B1 | * | 9/2001 | Durga et al. | 424/49 |
| 6,333,024 B1 | * | 12/2001 | Masters et al. | 424/49 |

* cited by examiner

*Primary Examiner*—Shep K. Rose
(74) *Attorney, Agent, or Firm*—Paul Shapiro

(57) ABSTRACT

A two component dental composition is disclosed which eliminates or substantially reduces the discomfort and pain associated with dentinal hypersensitivity which composition comprises a first dentifrice component having an alkaline pH and contains a potassium ion releasable compound and an alkali metal silicate, a second dentifrice component having an acid pH, the first and second components being maintained separate from each other until dispensed and combined for application to teeth requiring relief from dentine hypersensitivity, whereby heightened desensitization is experienced by the user.

18 Claims, No Drawings

DESENSITIZING DUAL COMPONENT DENTIFRICE

BACKGROUND OF THE INVENTION

1. Field of the Invention

The present invention relates to a desensitizing dentifrice composition which eliminates or reduces the discomfort and pain associated with dentinal hypersensitivity and more particularly to a two-component desensitizing dental composition containing potassium salt desensitizing agents.

2. The Prior Art

Dentinal hypersensitivity is defined as acute, localized tooth pain in response to physical stimulation of the dentine surface as by thermal (hot or cold) osmotic, tactile combination of thermal, osmotic and tactile stimulation of the exposed dentin.

Exposure of the dentine, which is generally due to recession of the gums, or loss of enamel, frequently leads to hypersensitivity. The art has determined that dentine tubules open to the surface have a high correlation with dentine hypersensitivity, Abs, J. Clin. Periodontal. 14,280–4 (1987). Dentinal tubules lead from the pulp to the cementum. When the surface cementum of the tooth root is eroded, the dentinal tubules become exposed to the external environment. The exposed dentinal tubules provide a pathway for transmission of fluid flow to the pulpal nerves, the transmission induced by changes in temperature, pressure and ionic gradients.

It is known to the art that potassium ion releasable compounds are effective in the treatment of dentinal hypersensitivity. For example, U.S. Pat. No. 3,863,006 discloses that toothpastes containing potassium salts such as potassium nitrate desensitize the teeth after tooth brushing for several weeks. It is believed by those skilled in the art that an elevation in the extracellular potassium concentration in the vicinity of pulpal nerves underlying sensitive dentin is responsible for the therapeutic desensitizing effect of topically applied oral products which contain potassium nitrate. Due to passive diffusion of potassium ion into and out of the open dentine tubules, repeated application of the active ingredient is necessary to build up the necessary concentration in the vicinity of the pulpal nerves.

It is believed that the improved pain relief is obtained from the use of potassium salts in combination with gradual mineralization on the dentin surface which can either totally or partially occlude dentin tubules. Total occlusion will dramatically reduce fluid flow within the tubules which stimulates pain. Partial occlusion of the dentin tubules is believed to increase delivery of potassium ion inside the tooth because the inward diffusive flux is less dependent upon tubule radius than outward fluid flow (due to positive pulpal pressures) (See DH Pashley and WG Mathews, Archs. Oral Biol. (1993) 38, 577–582). Therefore, this enhanced delivery of potassium should enhance relief.

In copending application U.S. Ser. No. 09/234,829 filed Jan. 21, 1999 there is disclosed a dual component dentifrice comprised of separately housed dentifrice components of acidic and alkaline pH, at least one component containing a potassium salt, the components being combined during use, the combined composition exhibiting improved effectiveness, when applied to the teeth, in obturating dentinal tubules with concomitant desensitization of teeth as compared to single component compositions of neutral pH.

Although the dentifrice composition of U.S. Ser. No. 09/234,829 is highly effective in the treatment of dentine hypersensitivity, the art continuously seeks means to improve the efficacy of such treatment.

SUMMARY OF THE INVENTION

In accordance with the present invention there is provided a method for the treatment of dentinal hypersensitivity using a multicomponent dentifrice comprised of two separately housed, semi-solid aqueous components; the first component containing, in an orally acceptable vehicle having an alkaline pH of at least about 8.5, and preferably about 9.0 to about 10.5, and containing an alkali metal silicate salt and a potassium ion releasable compound, the second component having an acid pH from about 2 to about 6 and preferably about 3 to about 5, whereby upon mixing and combination of the components, upon repeated application of the mixture to the teeth increased relief from dentinal hypersensitivity is experienced by the user.

DESCRIPTION OF THE PREFERRED EMBODIMENTS

In use, the components of the two component dentifrice of the present invention comprises a first alkaline dentifrice component containing the potassium ion releasable salt and an alkali metal silicate salt, and a second acidic dentifrice component containing a polymeric polycarboxylate compound. Both components are preferably formulated to have similar rheological characteristics, so that the two components may be simultaneously coextruded in the desired predetermined amounts when separately housed in a multi-compartmented tube or pump device.

To prepare the alkaline dentifrice component of the present invention, an alkaline agent is generally incorporated in the dentifrice component which normally includes a vehicle which contains water, humectant, surfactant and an abrasive. The pH of such dentifrice is in the alkaline range of about 8.5 to 10.5 and preferably about 9.0 to about 10.0. The acidic dentifrice component is prepared using a similar vehicle, the pH of such dentifrice being in the acid range of about 2 to about 6.0 and preferably about 3 to about 5.0.

The humectant used in the preparation of the dentifrice components is generally a mixture of humectants, such as glycerol, sorbitol and a polyethylene glycol of molecular weight in the range of 200 to 1000, but other mixtures of humectants and single humectants may also be employed. The humectant content is in the range about of 10% to about 80% by weight and preferably about 20 to about 50% by weight of the dentifrice component. The water content is in the range of about 10 to about 40% by weight and preferably about 20 to about 30% by weight.

Surfactants may be incorporated in the dentifrice components to provide foaming properties. The surface-active material is preferably anionic or nonionic in nature. Suitable examples of anionic surfactants are higher alkyl sulfates such as potassium or sodium lauryl sulfate which is preferred, higher fatty acid monoglyceride monosulfates, such as the salt of the monosulfated monoglyceride of hydrogenated coconut oil fatty acids, alkyl aryl sulfonates such as sodium dodecyl benzene sulfonate, higher fatty sulfoacetates, higher fatty acid esters of 1,2 dihydroxy propane sulfonate.

The surface active agent is generally present in the dentifrice component compositions of the present invention at a concentration of about 0.5 to about 10.0% by weight and preferably about 1.0 to about 5.0% by weight.

Abrasives may be incorporated in the dentifrice components of the present invention and preferred abrasives are siliceous materials, such as silica. A preferred silica is a precipitated amorphous hydrated silica, such as Sorbosil AC-35, marketed by Crosfield Chemicals, or Zeodent 115 from Huber Company but other abrasives may also be employed, including hydroxyapatite, sodium metaphosphate, potassium metaphosphate, tricalcium phosphate, calcium phosphate dihydrate, anhydrous dicalcium phosphate, calcium pyrophosphate, magnesium orthophosphate, trimagnesium phosphate, calcium carbonate, sodium bicarbonate, alumina trihydrate, aluminum silicate, calcined alumina and bentonite.

The concentration of abrasive in the dentifrice component compositions of the present invention will normally be in the range of 2 to about 40% by weight and preferably 5 to 25% by weight.

Inorganic and organic thickeners are also used in the preparation of the dentifrice components. Inorganic thickeners which may be included in the dentifrice components include amorphous silicas such as Zeodent 165 available from Huber Corporation, and Sylox 15 from W. R. Grace.

Organic thickeners of natural and synthetic gums and colloids may also be used to prepare the dentifrice components of the present invention. Examples of such thickeners are carrageenan (Irish moss), xanthan gum, sodium carboxymethyl cellulose, starch, polyvinylpyrrolidone, hydroxyethylpropylcellulose, hydroxybutyl methyl cellulose, hydroxypropyl methyl cellulose, and hydroxyethyl cellulose.

The inorganic thickener may be incorporated in the dentifrice components of the present invention at a concentration of about 0.5 to about 5% by weight and preferably about 1 to about 3% by weight. The organic thickener may be incorporated in the compositions of the present invention at a concentration of about 0.1 to about 3% by weight and preferably about 0.4 to about 1.5% by weight.

Alkaline agents such as alkali metal compounds including sodium hydroxide, potassium hydroxide, sodium bicarbonate, sodium carbonate are incorporated in the alkaline dentifrice component of the present invention in amounts in the range of about 0.5 to 15% by weight, preferably about 1.0 to about 8%. by weight and most preferably at about 1.0 to about 5.0% by weight of the component. Mixtures of the above alkali metal compounds may also be used. Sodium hydroxide is the preferred alkaline agent.

It is critical to the practice of the present invention that the pH of the alkaline dentifrice component be maintained at 8.5 or above in order to maintain the stability of the alkali metal silicate. When the alkaline and acid dentifrice components are mixed (as during brushing) there is believed the formation of a micronized silicate in situ as a result of the neutralization reaction. As well hereinafter be demonstrated, this silica deposit aids in the obturation of the exposed dentin tubules as measured by a reduction in the flow characteristics through dentin.

The source of alkali metal silicate present in the alkaline dentifrice component is generally a water soluble silicate salt such as $Na_2SiO_3$ and $Na_6Si_2O_7$. The silicate salt is incorporated in the alkaline dentifrice component at a concentration of about 0.5 to about 4.0% by weight. A sodium silicate salt having a $Na_2O:SiO_2$ ratio of 1:3 to 1:3.3 with a $SiO_2$ concentration of 27.7% to 29.4% is preferred in the practice of the present invention.

The source of desensitizing potassium ion releasable compound is generally a water soluble potassium salt including potassium nitrate, potassium citrate, potassium chloride, potassium bicarbonate and potassium oxalate with potassium nitrate being preferred. The potassium salt is incorporated in the dentifrice component at a concentration of about 0.5 to about 20% by weight and preferably about 3 to about 15% by weight.

The acidic dentifrice component of the dentifrice composition of the present invention, which is maintained physically separate from the alkaline dentifrice component until mixing before use, may contain an acid to adjust the pH of the component to an acid value.

Acidic compounds which may be present in the acidic component to adjust the pH to an acid level to include both mineral and organic acids, such as, sulfuric acid, hydrochloric acid, malic acid, alginic acid, citric acid, succinic acid, lactic acid, tartaric acid, potassium bitartrate, acid sodium citrate, phosphoric acid, and sodium acid phosphate.

Polymeric polycarboxylates are useful in the present invention examples of which are disclosed in U.S. Pat. Nos. 5,188,821 and 5,192,531; and include synthetic anionic polymeric polycarboxylates, such as 1:4 to 4:1 copolymers of maleic anhydride or acid with another polymerizable ethylenically unsaturated monomer, preferably methyl vinyl ether/maleic anhydride having a molecular weight (M.W.) of about 30,000 to about 1,000,000, most preferably about 30,000 to about 800,000. These polymers may be used in the form of their free acids or preferably partially or fully neutralized water-soluble alkali metal (e.g., potassium and preferably sodium) or ammonium salts. These copolymers are available for example as Gantrez, e.g., AN 139 (M.W. 500,000), AN 119 (M.W. 250,000) and preferably S-97 Pharmaceutical Grade (M.W. 700,000) available from ISP Technologies, Inc., Bound Brook, N.J. 08805.

Other operative polymeric polycarboxylates include linear and cross-linked polyacrylates and those disclosed in U.S. Pat. No. 3,956,480, such as the 1:1 copolymers of maleic anhydride with ethyl acrylate, hydroxyethyl methacrylate, N-vinyl-2-pyrrolidone, or ethylene, the latter being available for example as Monsanto EMA No. 1103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone.

Additional operative polymeric polycarboxylates include those disclosed in U.S. Pat. No. 4,138,477 and U.S. Pat. No. 4,183,914, such as copolymers of maleic anhydride with styrene, isobutylene or ethyl vinyl ether, polyacrylic, polyitaconic and polymaleic acids, and sulfoacrylic oligomers of molecular weight as low as 1,000, available as Uniroyal ND-2. The polymeric polycarboxylate is incorporated in the acid dentifrice component of the present invention in amounts ranging from 1.0 to about 5% by weight, and preferably about 4% by weight.

Fluoride providing salts having anticaries efficacy may also be incorporated in the dentifrice of the present invention and are characterized by their ability to release fluoride ions in water. It is preferable to employ a water soluble fluoride salt providing about 10–2,000 ppm of fluoride ion, and preferably about 1000–1500 ppm of fluoride ion. Among these materials are water soluble inorganic metal salts, for example, sodium fluoride, potassium fluoride, sodium monofluorophosphate, stannous fluoride and sodium fluorosilicate. Sodium fluoride, sodium monoflurophosphate and stannous fluoride are preferred fluoride providing salts.

Pyrophosphate salts having anticalculus efficacy may also be incorporated in the dentifrice of the present invention. Pyrophosphates useful in the practice of the present invention include water soluble salts such as dialkali or tetraalkali metal pyrophosphate salts such as $Na_4P_2O_7$ (TSPP), $K_4P_2O_7$, $Na_2K_2P_2O_7$, $Na_2H_2P_2O_7$ and $K_2H_2P_2O_7$. Polyphosphates are also useful anticalculus agents and include water soluble alkali metal tripolyphosphates such as sodium tripolyphosphate and potassium tripolyphosphate and sodium hexametaphosphate.

The pyrophosphate salts are incorporated in the dentifrice composition of the present invention at a concentration of about 0.5 to about 2.0% by weight, and preferably about 1.5 to about 2% by weight and the polyphosphate salts are incorporated in the dentifrice composition of the present invention at a concentration of about 1.0 to about 7.0% by weight.

Colorants such as pigments and dyes may be used in the practice of the present invention. Pigments include nontoxic, water insoluble inorganic pigments such as titanium dioxide and chromium oxide greens, ultramarine blues and pinks and ferric oxides as well as water insoluble dye lakes prepared by extending calcium or aluminum salts of FD&C dyes on alumina such as FD&C Green #1 lake, FD&C Blue #2 lake, FD&C R&D #30 lake and FD&C #Yellow 15 lake. The pigments have a particle size in the range of 5–1000 microns, preferably 250–500 microns, and are present at a concentration of 0.5 to 3% by weight.

Dyes used in the practice of the present invention are generally food color additives presently certified under the Food Drug & Cosmetic Act for use in the food and ingested drugs, including dyes such as FD&C Red No. 3 (sodium salt of tetraiodofluorescein), FD&C Yellow No. 5 (sodium salt of 4-p-sulfophenylazo-1-p-sulfophenyl-5-hydroxypyrazole-3 carboxylic acid), FD&C Yellow No. 6 (sodium salt of p-sulfophenylazo-B-naphtol-6-monosulfonate), FD&C Green No. 3 (disodium salt of 4-{ [4-(N-ethyl-p-sulffobenzylamino)-phenyl]-(4-hydroxy-2-sulfoniumphenyl)-mewthylene } -[1-(N-ethyl-N-p-sulfobenzyl)-Δ-3,5-cyclohexadienimine], FD&C Blue No. 1 (disodium salt of dibenzyldiethyldiaminotriphenylcarbinol trisulfonic acid of indigotin) and mixtures thereof in various proportions. The concentration of the dye for the most effective result in the present invention is present in the dentifrice composition in an amount from about 0.0005 percent to about 2 percent of the total weight.

A striped dentifrice product may be obtained using the dual component dentifrice of the present invention, wherein colorants of contrasting colors are incorporated in each of the dentifrice components to be dispensed; the colorants being pharmacologically and physiologically non-toxic when used in the suggested amounts. Colorants used in the practice of the present invention include both the pigments and dyes discussed above.

Any suitable flavoring or sweetening material may also be incorporated in the dentifrice composition of the present invention. Examples of suitable flavoring constituents are flavoring oils, e.g., oils of spearmint, peppermint, wintergreen, sassafras, clove, sage, eucalyptus, marjoram, cinnamon lemon, and orange, and methyl salicylate. Suitable sweetening agents include sucrose, lactose, maltose, sorbitol, xylitol, sodium cyclamate, perillatine, and sodium saccharin. Suitably, flavor and sweetening agents may together comprise from 0.01% to 5% or more of the preparations.

To prepare either of the dentifrice components of the present invention, generally the humectants e.g. glycerin, propylene glycol, polyethylene glycol ingredients, are dispersed with any organic thickeners, sweetener, pigments such as titanium dioxide and any phosphate salts included as anti-calculus ingredients. Water is then added into this dispersion along with any anticalculus agents. In the first component, the potassium ion releasing salt, alkali metal silicate and an alkaline agent such as sodium hydroxide is added. In the second component the polymeric polycarboxylate is added and an ingredient to lower the pH to an acid level may also be added. These ingredients are mixed until a homogenous phase is obtained for each component. Thereafter inorganic thickener, silica abrasive, flavor and surfactant ingredients are added and the ingredients mixed at high speed under vacuum of from about 20 to 100 mm of Hg. The resultant product is in the case of each component is a homogeneous, semi-solid, extrudible paste product.

The multicomponent dentifrice composition of the present invention is packaged in a suitable dispensing container in which the components are maintained physically separated and from which the separated components may be dispensed synchronously as a combined ribbon for application to a toothbrush. Such containers are known in the art. An example of such a container is a two compartment dispensing container, such as a pump or a tube, having collapsible sidewalls, as disclosed in U.S. Pat. No. 4,487,757 and 4,687,663; wherein, the tube body is formed from a collapsible plastic web such as polyethylene or polypropylene and is provided with a partition within the container body defining separate compartments in which the physically separated components are stored and from which they are dispensed through a suitable dispensing outlet.

The following example is further illustrative of the present invention, but it is understood that the invention is not limited thereto. All amounts and proportions referred to herein and in the appended claims are by weight, unless otherwise stated.

EXAMPLE

A two component (Components A and B) desensitizing dentifrice of the present invention was prepared, designated Dentifrice I, Component A, a paste having an alkaline pH and containing potassium nitrate and sodium silicate ($Na_2O:SiO_2$ ratio 1:3.22) and a Component B, a gel having an acid pH. The ingredients and pH of Components A and B are listed in Table I, below.

TABLE I

Dentifrice I

| Component Ingredients | Weight % A Alkaline paste | B Acidic gel |
|---|---|---|
| Deionized Water | 32.577 | 17.117 |
| Sodium Fluoride | 0.243 | 0.243 |
| Sodium silicate | 3.0 | — |
| Potassium Nitrate | 10.000 | — |
| Gantrez S-97 (13% solution) | — | 15.0 |
| Glycerin | 25.48 | 17.00 |
| Sorbitol (70% solution) | — | 20.00 |
| Polyethylene glycol 600 | 3.000 | — |
| Xanthan | 0.700 | 0.40 |
| Carboxymethyl cellulose | 0.500 | 0.500 |
| Sodium saccharin | 0.400 | 0.400 |
| Titanium Dioxide | 2.000 | — |
| Tetrasodium pyrophosphate | — | 0.50 |
| Sodium Hydroxide (50%) | 0.50 | — |
| FD&C Blue #1 (1% solution) | — | 0.24 |
| Zeodent 115 | 15.000 | 23.00 |
| Zeodent 165 | 2.000 | 3.000 |

TABLE I-continued

Dentifrice I

| Component Ingredients | Weight % A Alkaline paste | B Acidic gel |
|---|---|---|
| Sodium Bicarbonate | 2.000 | — |
| Sodium lauryl sulfate | 1.500 | 1.500 |
| Flavor | 1.1 | 1.100 |
| Total | 100 | 100 |
| pH (as is) | 9.0 | 5.0 |

In the preparation of Dentifrice I, the glycerin, polyethylene glycol and organic thickeners were dispersed in a conventional mixer until the mixture became a slurry, which was smooth in appearance. Color and sweetener were dispersed in this slurry before the addition of water. In the preparation of Component A, potassium nitrate and sodium silicate were then dispersed in this slurry. In the preparation of Component B,. Gantrez S-97 was then dispensed in the gel phase in sufficient amount to acidify the gel. This mixture was mixed for 20 to 30 minutes producing a homogeneous gel phase to acidify the gel. The mixture was added to a vacuum mixer and cooled below 105° F. Zeodent 115, Zeodent 165 and sodium bicarbonate were then added and mixed for 10 to 30 minutes at high speed under a vacuum of about 50 mm Hg, providing a homogenous mixture. The sodium lauryl sulfate and flavor were then added to the individual dentifrice components which was followed by mixing another 5–15 minutes under vacuum of 50 mm Hg to prepare the resultant component product.

The desensitizing efficacy of the two component composition described above was evaluated using dentin disks of 750 μm thickness cut from extracted human molars. The disks were prepared for treatment by etching with 6% citric acid for 2 minutes to remove any surface smear.

The rate of flow of a phosphate buffer solution (0.2 mm phosphate, 0.2 mm $CaCl_2$ and 0.1M NaCl at pH=7) through the disks under 70mm water pressure were measured to determine baseline flow rates, the disks being divided into groups of three each such that the average flow rates between the groups were similar.

The dentin disks were then treated by brushing for a 45 second period with the combined components of Dentifrice I at a 1:1 volume ratio. The pH of the combined components was about 9.5 when diluted 1:1 with deionized water. As a control, the procedure of the Example was repeated using the phosphate buffer solution as the treatment which treatment was designated "Control".

The treated disks were immersed in 10–25 ml of tap water and agitated with the end of a toothbrush to remove dentifrice from the disk surface. The disks were put into the phosphate buffer solution between brushings. The disks were treated twelve (12) times each over a four day period.

The flow rate of the phosphate buffer solution under 70 milligrams of artificial saliva per second (mgs) was determined at this pressure which flow rates are recorded in Table II below.

The artificial saliva (pH=7) had the following composition:

| Phosphate ion | 0.2 mM (millimole) |
|---|---|
| $CaCl_2$ | 1.06 mM |
| NaCl | 0.150 mM |
| pH | 7.4 |

The extent of obturation was measured by the fluid flow rate method. Lower fluid flow rates generally indicates greater obturation of the dentin tubules

TABLE II

| Treatment | Average Flow (mg/s)* |
|---|---|
| 1. Dentifrice I | 0.443 |
| 2. Control | 1.53 |

*Average of 3 replicates

The flow rates of artificial saliva solution through the dentin disks recorded in Table II indicate that Dentifrice I has a pronounced effect on reducing flow relative to the phosphate buffer solution Control. The reductions in flow are believed to be due to occlusion of the dentinal tubules. The occlusive state produced by the Dentifrice I treatment is considered by the art to be predictive of clinical dentinal hypersensitivity reduction (M. Brannstrom and A. Astrom, J. Dent. Res. (1964) 43, 619. 625.

The treated disks which were subjected to the flow measurements were subjected to silicon analyses by Electron Spectroscopy for Chemical Analysis (ESCA). Before these analysis were conducted, the disks were rinsed with deionized water to remove the phosphate buffer solution and dried. The silicon analysis results are recorded in Table In below.

TABLE III

| | ESCA | |
|---|---|---|
| Treatment | | Si Atomic Percent |
| Dentifrice I | | 7.1 |
| Phosphate buffer solution | | 0.2 |

These results recorded in Table II indicate that the amount of silica formed on the surface of the dentin disks treated with the combined components of Dentifrice I is substantially greater than the disks treated with the phosphate buffer control. The atomic percentages of Si present in the dentin surfaces treated with Dentifrice I are indicative of high deposits of silica.

The flow data and the ESCA data of Tables II and III both provide evidence that the unique combination of the dentifrice components of the present invention effects an unexpected substantial improvement in the remediation of dentinal hypersensitivity.

What is claimed is:

1. A two component dental composition which eliminates or substantially reduces the discomfort and pain associated with dentinal hypersensitivity which composition comprises a first dentifrice component having an alkaline pH and contains a potassium ion releasable compound and an alkali metal silicate, and a second dentifrice component having an acid pH, the first and second components being maintained separate from each other until dispensed and combined for application to teeth requiring relief from dentine hypersensitivity, whereby heightened desensitization is experienced by the user.

2. The composition of claim 1 wherein the potassium ion releasable compound is a water soluble potassium salt.

3. The composition of claim 2 wherein the potassium salt is potassium nitrate.

4. The composition of claim 2 wherein the alkali metal silicate is sodium silicate.

5. The composition of claim 1 wherein the alkaline dentifrice component is an aqueous paste having a pH of about 8.5 to about 10.5.

6. The composition of claim 1 wherein the pH of the alkaline dentifrice component is adjusted with sodium hydroxide.

7. The composition of claim 1 wherein the acidic dentifrice component is an aqueous gel having a pH of about 2.0 to about 6.0.

8. The composition of claim 1 wherein the acidic dentifrice component contains a polymeric polycarboxylate compound.

9. The composition of claim 8 wherein the polymeric polycarboxylate is a vinyl ether/maleic anhydride copolymer.

10. A method for eliminating or reducing the discomfort and pain associated with dentinal hypersensitivity which comprises preparing (1) a first dentifrice component having an alkaline pH and contains a potassium ion releasable compound and an alkali metal silicate and (2) a second dentifrice component having an acid pH, separately housing the first and second components, dispensing the first and second components and combining the dispensed components for application to teeth requiring relief from dentine hypersensitivity and thereafter applying the combined components to the teeth whereby heightened desensitization is experienced by the user.

11. The method of claim 10 wherein the potassium ion releasable compound is a water soluble potassium salt.

12. The method of claim 10 wherein the potassium salt is potassium nitrate.

13. The method of claim 9 wherein the alkali metal silicate is sodium silicate.

14. The method of claim 10 wherein the alkaline dentifrice component is an aqueous paste having a pH of about 8.5 to about 10.5.

15. The method of claim 10 wherein the pH of the alkaline dentifrice component is adjusted to an alkaline pH with sodium hydroxide.

16. The method of claim 10 wherein the acidic dentifrice component is an aqueous dentifrice having a pH of about 2.0 to about 6.0.

17. The method of claim 10 wherein the acidic dentifrice component contains a polymeric polycarboxylate compound.

18. The method of claim 17 wherein the polymeric polycarboxylate compound is a vinyl ether/maleic anhydride copolymer.

* * * * *